United States Patent [19]

Hegg

[11] Plant 4,164

[45] Dec. 13, 1977

[54] POINSETTIA PLANT

[75] Inventor: Thormod Hegg, Reistad, Norway

[73] Assignee: Paul Ecke, Jr., Encinitas, Calif.

[21] Appl. No.: 722,221

[22] Filed: Sept. 10, 1976

[51] Int. Cl.[2] ..... A01H 5/00

[52] U.S. Cl. ..... Plt./86

[58] Field of Search ..... Plt./86

[56] References Cited

U.S. PATENT DOCUMENTS

P.P. 3,392 8/1973 Ecke ..... Plt./86

*Primary Examiner*—Robert E. Bagwill

*Attorney, Agent, or Firm*—Frank B. Robb

[57] ABSTRACT

There is disclosed a new variety of Poinsettia Plant characterized by the short growing and compact plant habit, with a uniform and fast rooting habit, self branching plants with production of multiple blooms without pinching off the terminal buds brighter red bracts than the red bracts of U.S. Plant Pat. No. 2,962, "Annette Hegg", the bract color retaining the brillance much longer when plants are used for home decoration, the production of more and heavier side shoots when grown as a single stem plant which makes them valuable from a commercial standpoint since cuttings are likely to be produced thereby.

1 Drawing Figure

The present invention relates to a new and distinct variety of Poinsettia plant (botanically known as *Euphorbia pulcherrima*) which was discovered by me as a sport of the red poinsettia variety "Annette Hegg" (U.S. Plant Pat. No. 2,962), and which instant variety I designate as "Annette Hegg Top Star".

At the time of my discovery aforesaid, I was growing many poinsettias of various varieties including those of the variety "Annette Hegg" at my greenhouses at Reistad, Norway, my attention being attracted to a particular plant among those of "Annette Hegg" which bore bracts of a substantially brighter red color than the normal red bracts of "Annette Hegg".

Upon close inspection of this particular plant, I determined that it had sported, so I carefully preserved the sport keeping it under very close observation.

In due course, I asexually reproduced this sport by vegetative cuttings taken therefrom and planted in my greenhouses at Reistad, Norway.

Continuing the observation and tests prevailing in respect to the original sport, and its progeny as is my custom, the progeny being derived from vegetative cuttings aforesaid, and which have been propagated successfully through several generations, I was able to fully confirm that the bright red bracts come true and remain very stable.

While many observations and tests disclose that for most purposes the new sport generally resembles the parent variety "Annette Hegg", except for its brighter red bract color, I have also found that the brighter red bract color of the sport retains its brilliance much longer when the plants are grown in the home after removal from the greenhouse, than the bracts of "Annette Hegg" which tend to fade rather quickly.

A further interesting and distinguishing feature of the new variety is the fact that it produces many side shoots when the plant is not pinched.

The various characteristics and distinctions referred to above represent a unique and commercially valuable combination of features thereby distinguishing the sport from its parent variety as well as from all other poinsettia varieties of which I am aware, and further are evidenced by the following summary of characteristics which are outstanding in this new sport:

1. A short-growing and compact plant habit;
2. A uniform and fast rooting habit;
3. A self-branching habit resulting in the production of multiple blooms without pinching off the terminal buds as required for many other poinsettia varieties;
4. Attractive green foliage which is very similar in color to the foliage of "Annette Hegg";
5. Attractive, brighter red bracts than the normal red bracts of "Annette Hegg", and the bright red color of the bracts being more stable and retaining its brilliance much longer when the plants are used for home decoration; and
6. Long-lasting plant qualities.

The accompanying drawing shows a typical specimen plant of my new poinsettia variety as depicted in color as nearly true as it is reasonably possible to make the same in a color illustration of this character.

Although the details of my new poinsettia sport, except for the principal differences referred to in the foregoing, are generally similar to those described in U.S. Plant Pat. No. 2,962 to which reference may be readily had, the following brief description is given for convenience, with color terminology in accordance with Wilson's Horticultural Colour Chart, except where general color terms of ordinary dictionary significance are obvious:

Parentage: Sport of "Annette Hegg" (U.S. Plant Pat. No. 2,962).

Propagation: Holds its distinguishing characteristics through succeeding propagations by vegetative cuttings.

Form: Short-growing; compact.

Habit of growth: Self-branching; does not require pinching to produce multiple blooms.

Rooting habit: Very uniform and very fast.

Blooming habit: 9-week variety.

Blooming season: Blooms predictably and in time for Christmas season and beyond; also good for flowering in spring, summer and autumn.

Foliage:

*Shape.*—Similar to "Annette Hegg".

*Color.*—Similar to "Annette Hegg".

Bracts: Obovate; relatively broad; brighter and retains brilliance longer.

*Color.*—Near Blood Red, Plate 820/2.

Flowers: (Cyathia): Early; numerous; strong; little if any tendency to split; do not drop off prematurely.

Reproductive organs:

*Stamens.*—Quite numerous; from about ⅛ inch to ¼ inch long. Color — Near Currant Red, Plate 821/2.

*Pollen.*—Strong. Color — Near Canary Yellow, Plate 2.

*Styles.*—Color — Near Blood Red, Plate 820.

*Ovaries.*—Color — Near Scheele's Green, Plate 860/1.

*Nectar cups.*—Color — Near Lemon Yellow, Plate 4/1.

General Observations: While this new sport generally resembles the variety of "Annette Hegg", U.S. Plant Pat. No. 2,962, it is principally distinguished therefrom by its brighter red bracts which retain their brilliance much longer and with much less tendency to fade when grown under the same conditions as "Annette Hegg", U.S. Plant Pat. No. 2,962. In addition, this sport produces more side shoots, when it is grown as a single stem, unpinched plant, than is usually found in other poinsettia varieties.

In comparison with "Annette Hegg Supreme" U.S. Plant Pat. No. 3,392, my new variety is of a bright red somewhat less brillant than "Supreme" when viewed under fluorescent light but brighter than U.S. Plant Pat. No. 2,962. My new variety produces more and heavier side shoots when grown as a single stem plant than "Annette Hegg Supreme" as well as more than "Annette Hegg" U.S. Plant Pat. No. 2,962. Further the blooming time of my new variety is less than "Annette Hegg Supreme" as well as U.S. Plant Pat. No. 2,962 and when considered from a commercial standpoint even a few days is very important.

I claim:

1. A new and distinct variety of Poinsettia plant, substantially as herein shown and described, characterized particularly as to novelty by the unique combination of short-growing and compact plant habit, uniform and fast rooting habit, a self-branching habit resulting in the production of multiple blooms without pinching off the terminal buds, good green foliage, attractive brighter red bracts than the normal red bracts of U.S. Plant Pat. No. 2,962, "Annette Hegg", the color of the bracts being more stable and retaining its brilliance much longer when the plants are used for home decoration, and long lasting plant qualities.

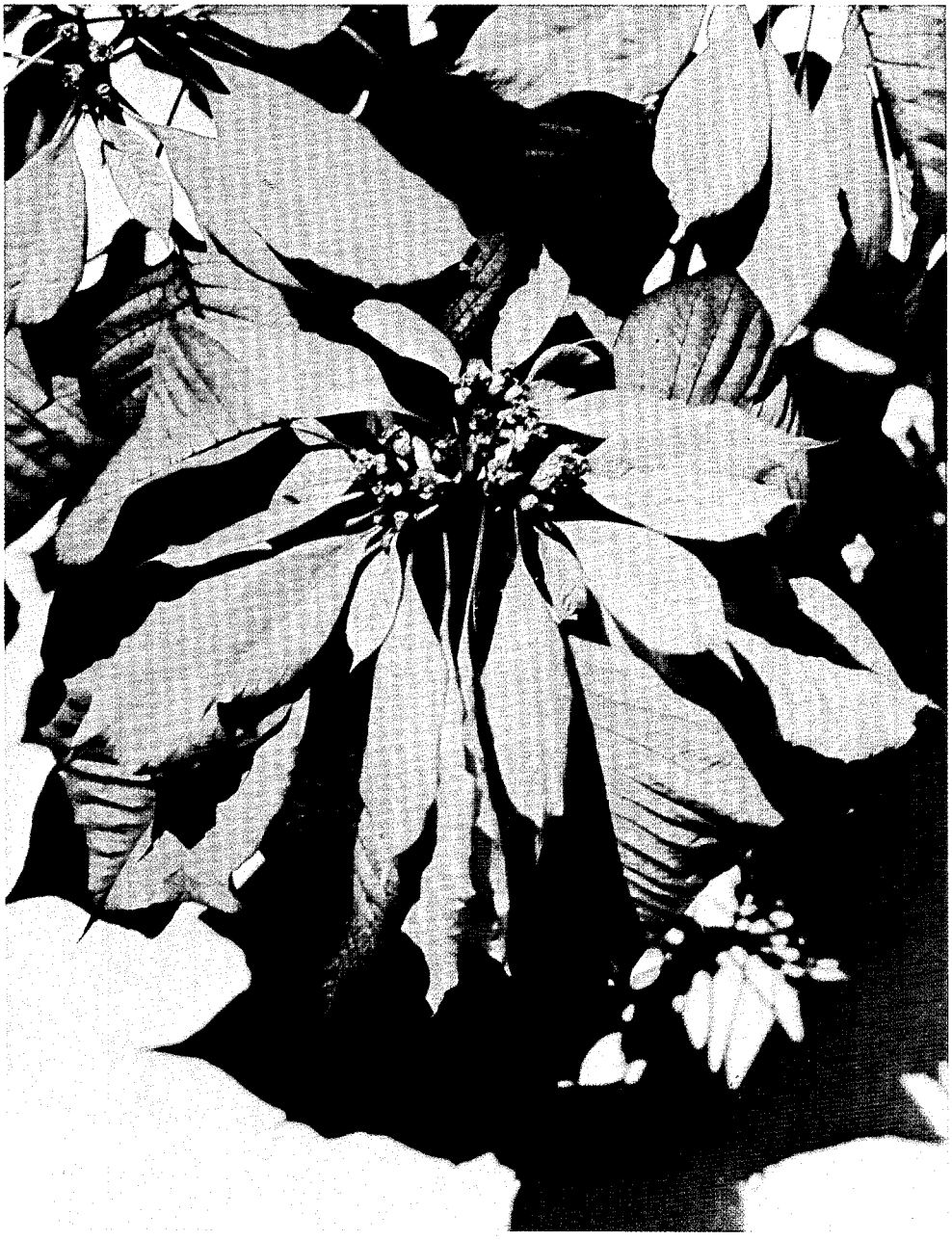

* * * * *